(12) United States Patent
Van Broekhoven et al.

(10) Patent No.: US 7,750,197 B2
(45) Date of Patent: *Jul. 6, 2010

(54) ALKYLATION PROCESS USING A CATALYST COMPRISING A SOLID ACID AND A HYDROGENATION METAL

(75) Inventors: Emanuel Hermanus Van Broekhoven, Monnickendam (NL); Jan Sant, Utrecht (NL); Stephan Zuijdendorp, Heemskerk (NL); Niels Winkler, Utrecht (NL)

(73) Assignee: Albemarle Netherlands B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/588,106

(22) PCT Filed: Jan. 26, 2005

(86) PCT No.: PCT/EP2005/000929

§ 371 (c)(1),
(2), (4) Date: Jun. 5, 2007

(87) PCT Pub. No.: WO2005/075387

PCT Pub. Date: Aug. 18, 2005

(65) Prior Publication Data

US 2007/0282149 A1    Dec. 6, 2007

Related U.S. Application Data

(60) Provisional application No. 60/547,923, filed on Feb. 26, 2004.

(30) Foreign Application Priority Data

Feb. 9, 2004    (EP) .................................. 04075387

(51) Int. Cl.
*C07C 2/58*    (2006.01)
*C07C 2/62*    (2006.01)

(52) U.S. Cl. ........................ 585/722; 585/727; 585/730; 585/906

(58) Field of Classification Search ................. 585/906, 585/722, 727, 730
See application file for complete search history.

(56) References Cited

U.S. PATENT DOCUMENTS

| | | | | |
|---|---|---|---|---|
| 3,534,115 A | * | 10/1970 | Bushick | 585/476 |
| 3,644,565 A | * | 2/1972 | Biale | 585/722 |
| 4,300,015 A | | 11/1981 | Kirsch et al. | |
| 4,918,255 A | * | 4/1990 | Chou et al. | 585/331 |
| 4,992,616 A | | 2/1991 | Chou et al. | |

FOREIGN PATENT DOCUMENTS

| | | |
|---|---|---|
| EP | 0 456 839 B1 | 8/1994 |
| EP | 0 842 914 B1 | 12/2002 |
| EP | 1 308 207 A2 | 5/2003 |
| WO | WO-01/91901 A1 | 12/2001 |

* cited by examiner

*Primary Examiner*—Thuan Dinh Dang
(74) *Attorney, Agent, or Firm*—Jeremy J. Kliebert

(57) ABSTRACT

The invention relates to a process for alkylating a hydrocarbon feed which comprises contacting the hydrocarbon feed to be alkylated with an alkylation agent in the presence of a catalyst comprising a solid acid, a hydrogenation metal, and 1.5-6 wt % of water, measured as the loss on ignition at 600° C. The presence of 1.5-6 wt % of water results in a higher activity and a higher alkylate quality compared with a comparable but drier catalyst.

10 Claims, 2 Drawing Sheets

Figure 1:
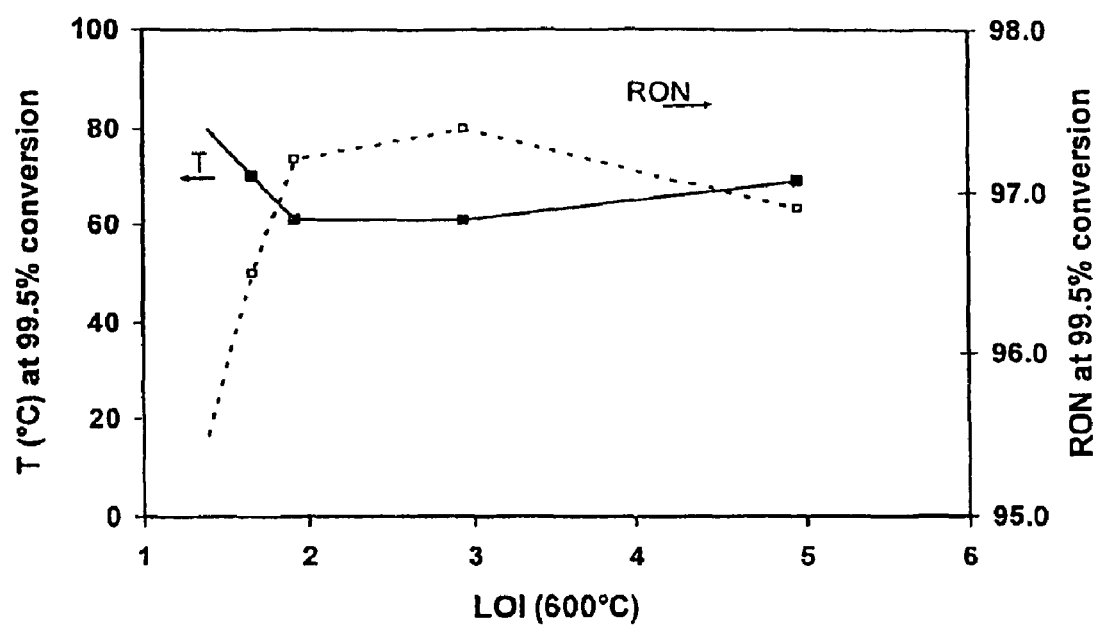

ALKYLATION PROCESS USING A CATALYST COMPRISING A SOLID ACID AND A HYDROGENATION METAL

This application is the National Stage of International Patent Application PCT/EP2005/000929 filed on Jan. 26, 2005, which application claims priority from EP Application No. 04075387.3, filed Feb. 9, 2004, and U.S. Provisional Application No. 60/547,923, filed Feb. 26, 2004, the disclosures of which are incorporated herein by reference.

The present invention relates to a process for alkylating a hydrocarbon feed which comprises contacting the hydrocarbon feed to be alkylated with an alkylation agent in the presence of a catalyst comprising a solid acid and a hydrogenation metal.

Within the framework of the present invention, the term alkylation refers to the reaction of an alkylatable compound, such as an aromatic or saturated hydrocarbon, with an alkylation agent, such as an olefin. Without limiting the scope of the invention, we will further illustrate the invention by discussing the alkylation of saturated hydrocarbons, in general branched saturated hydrocarbons, with an olefin to give highly branched saturated hydrocarbons with a higher molecular weight. Hydrocarbons contain no atoms other than hydrogen and carbon.

This reaction is of interest because it makes it possible to obtain, through the alkylation of isobutane with an olefin containing 2-6 carbon atoms, an alkylate which has a high octane number and which boils in the gasoline range. Unlike gasoline obtained by cracking heavier petroleum fractions such as vacuum gas oil and atmospheric residue, gasoline obtained by alkylation is essentially free of contaminants such as sulfur and nitrogen and so has clean burning characteristics. Its high anti-knock properties, represented by the high octane number, lessen the need to add environmentally harmful anti-knock compounds such as aromatics or lead. Also, unlike gasoline obtained by reforming naphtha or by cracking heavier petroleum fractions, alkylate contains few if any aromatics or olefins, which, environmentally speaking, is a further advantage.

The alkylation reaction is acid-catalyzed. At present, in commercial alkylation equipment use is made of liquid acid catalysts such as sulfuric acid and hydrogen fluoride. The use of such catalysts is attended with a wide range of problems. For instance, sulfuric acid and hydrogen fluoride are highly corrosive, so that the equipment used has to meet high quality requirements. Since the presence of highly corrosive materials in the resulting fuel is objectionable, the remaining acid has to be removed from the alkylate. Also, because of the phase separations which have to be carried out, the process is complicated and thus expensive. Besides, there is always the risk that toxic substances such as hydrogen fluoride will be emitted.

A newer development in this field is the use of solid acid catalysts, such as zeolite-containing catalysts. WO 98/23560 discloses the use of a catalyst containing a zeolite, such as a Y-zeolite, a Group VIII noble metal, e.g. platinum or palladium, as hydrogenation metal, and optionally a matrix material, such as alumina, in the alkylation of hydrocarbons.

In contrast to the alkylation of aromatic hydrocarbons, in the alkylation of saturated hydrocarbons hydrogen transfer is the rate determining step. Hence, catalysts for the alkylation of saturated hydrocarbons require a hydrogenation metal.

It has now been surprisingly found that the use of a catalyst comprising a solid acid and a hydrogenation metal and which additionally contains 1.5-6 wt % of water—measured as the loss on ignition (LOI) at 600° C. and based on the total weight of the catalyst composition—results in a higher activity and a higher alkylate quality compared with a comparable but drier catalyst.

The Catalyst

The catalyst, when used in the alkylation process, comprises 1.5-6 wt % water. Preferably, the water content of the catalyst is 1.8-4 wt %, more preferably 2-3 wt %.

The water content of the catalyst is its water content during use in the alkylation process and is measured by determining the weight loss upon heating the catalyst for two hours at 600° C. ($LOI_{600}$).

The catalyst to be used in the process according to the invention further comprises a hydrogenation metal. Examples of suitable hydrogenation metals are constituents of the transition metals, such as metals of Group VIII of the Periodic Table, and mixtures thereof. Among these, noble metals of Group VIII of the Periodic Table are preferred. Platinum, palladium, and mixtures thereof are especially preferred. The amount of hydrogenation metal will depend on its nature. When the hydrogenation metal is a noble metal of Group VIII of the Periodic Table, the catalyst generally will contain in the range of 0.01 to 2 wt. % of the metal, preferably 0.1-1 wt. %, calculated as metal and based on the total weight of the catalyst.

The catalyst further comprises a solid acid. Examples of solid acids are zeolites such as zeolite beta, MCM-22, MCM-36, mordenite, X-zeolites and Y-zeolites, including H—Y-zeolites and USY-zeolites, non-zeolitic solid acids such as silica-alumina, sulfated oxides such as sulfated oxides of zirconium, titanium, or tin, mixed oxides of zirconium, molybdenum, tungsten, phosphorus, etc., and chlorinated aluminium oxides or clays. Preferred solid acids are zeolites, including mordenite, zeolite beta, X-zeolites and Y-zeolites, including H—Y-zeolites and USY-zeolites. Mixtures of solid acids can also be employed. An even more preferred solid acid is Y-zeolite with a unit cell size of 24.34-24.72 angstroms, while Y-zeolite with a unit cell size of 24.42-24.56 angstroms is preferred most.

The catalyst may additionally comprise a matrix material. Examples of suitable matrix materials are alumina, silica, titania, zirconia, clays, and mixtures thereof. Matrix materials comprising alumina are generally preferred.

Preferably, the catalyst comprises 2-98 wt % of the solid acid and 98-2 wt % of the matrix material, based on the total weight of the solid acid and the matrix material present in the catalyst. More preferably, the catalyst comprises 10-90 wt % of the solid acid and 90-10 wt % of the matrix material, based on the total weight of the solid acid and the matrix material contained in the catalyst. Even more preferably, the catalyst comprises 10-80 wt % of matrix material and balance solid acid, most preferably it comprises 10-40 wt % of the matrix material and balance solid acid, based on the total weight of the solid acid and the matrix material contained in the catalyst.

The catalyst preferably contains no halogen component.

Preferably, the catalyst comprises catalyst particles wherein the ratio between (i) the volume in catalyst pores with a diameter of 40-8,000 nm (in the following "macropores") and (ii) the specific length of the catalyst particles is in the range of 0.01-0.90 ml/(g*mm) and wherein the catalyst has a total pore volume of at least 0.20 ml/g.

The specific length of a catalyst particle is defined as the ratio between the geometric volume and the geometric surface of the solid part of this catalyst particle. The determination of the geometric volume and the geometric surface is known to the person skilled in the art and can be carried out, e.g., as described in DE 2354558.

The macropore volume as well as the total pore volume is determined via mercury intrusion on the basis of the Washburn equation covering pores with a diameter of 3.6-8,000 nm.

Preferably, the ratio between the volume in macropores and the specific length is above 0.20 ml/(g*mm), more preferably above 0.30 ml/(g*mm), and even more preferably above 0.40 ml/(g*mm), as well as preferably below 0.80 ml/(g*mm).

It is further preferred that the catalyst has a total pore volume of at least 0.23 ml/g and most preferably of at least 0.25 ml/g.

The catalyst particles comprised in the catalyst preferably have a specific length of at least 0.10 mm, more preferably of at least 0.16 mm, and most preferably of at least 0.20 mm. The upper limit of the specific length preferably lies at 2.0 mm, more preferably at 1.0 mm, and most preferably at 0.6 mm.

The volume in macropores preferably is at least 0.05 ml/g, most preferably at least 0.08 ml/g, and preferably below 0.30 ml/g, most preferably below 0.25 ml/g.

The particles of the catalyst can have many different shapes, including spheres, cylinders, rings, and symmetric or asymmetric polylobes, for instance tri- and quadrulobes. Preferably, the catalyst particles have an average particle diameter of at least 0.5 mm, more preferably of at least 0.8 mm, and most preferably of at least 1.0 mm. The upper limit of the average particle diameter preferably lies at 10.0 mm, more preferably at 5.0 mm, even more preferably at 3.0 mm.

Preparation of the Catalyst

The catalyst used in the process according to the invention is prepared by adjusting the water content of an existing catalyst comprising a solid acid and a hydrogenation metal.

The existing catalyst can be prepared by processes common to the industry. These will comprise, say, shaping the solid acid constituent after mixing it with a matrix material, to form carrier particles, followed by calcination of the particles. The hydrogenating function may, e.g., be incorporated into the catalyst composition by impregnating the carrier particles with a solution of a hydrogenation metal component.

After impregnation the catalyst is preferably calcined.

The catalyst is reduced at a temperature preferably in the range 200 to 500° C., more preferably 250 to 350° C., in a reducing gas such as hydrogen. This reduction can be performed before adjustment of the water content, after addition of water to the catalyst and/or by using reduction as a way to adjust the water content (see below). Preferably, the reduction is performed before adjustment of the water content. More preferably, the reduction is performed after drying the catalyst in a dry, non-reducing gas ($N_2$, He, air, etc.).

The water content of the catalyst can be adjusted by various methods. Such methods are exemplified below as methods 1, 2, and 3.

Method 1 involves increasing the LOI of a catalyst by exposing the catalyst to water before its use in the alkylation process, i.e. before contacting the catalyst with the hydrocarbon feed and the alkylation agent. This can be achieved by exposing the catalyst to a water-containing atmosphere—e.g. air—at, e.g., ambient conditions. Embodiments of this method include:

exposing a reduced catalyst to water until the desired LOI is reached, exposing an unreduced catalyst to water until an LOI above the desired level is reached, followed by reduction of the catalyst, thereby decreasing the LOI to the desired level, exposing a reduced catalyst to water until an LOI above the desired level is reached, followed by treatment of the catalyst in either an inert or a reducing atmosphere, thereby decreasing the LOI to the desired level, and reducing the catalyst in a hydrogen and water-containing atmosphere.

The reduction and exposure to water can be conducted in situ or ex situ. With in situ reduction and exposure to water, the catalyst is reduced and contacted with a water-containing atmosphere while being present in the reactor used for the alkylation process. This reduction and exposure to water is done before starting the alkylation process, i.e. before contacting the catalyst with the hydrocarbon feed and the alkylation agent.

Ex situ reduction and exposure to water requires transportation of the catalyst with the desired LOI to the reactor in which alkylation will take place.

In another embodiment, the catalyst can be contacted with water ex situ, while the subsequent reduction to reach the desired LOI is conducted in situ.

Method 2 involves decreasing the LOI of an existing catalyst to the desired level by reducing an unreduced catalyst with an LOI above the desired level before its use in the alkylation process, i.e. before contacting the catalyst with the hydrocarbon feed and the alkylation agent. Again, this reduction can be performed ex situ, i.e. outside the alkylation reactor, or in situ, i.e. inside the alkylation reactor.

Method 3 involves in-situ water addition by starting the alkylation process with a catalyst having an LOI below the desired level and adding water to the alkylation unit during processing, for instance by adding water to the hydrocarbon feed, by regenerating the catalyst in a water-containing atmosphere and/or by exposing the regenerated catalyst to a water-containing atmosphere.

A combination of two or more of the above methods is also possible. In particular, it is possible to adjust the LOI of the catalyst to the desired before the alkylation process is started (method 1 or 2) and re-adjust it after or during regeneration of the catalyst according to method 3.

The Alkylation Process

Preferably, the hydrocarbon to be alkylated in the alkylation process is a branched saturated hydrocarbon such as an isoalkane having 4-10 carbon atoms. Examples are isobutane, isopentane, isohexane or mixtures thereof, with isobutane being most preferred. The alkylation agent preferably is an olefin having 2-10 carbon atoms, more preferably 2-6 carbon atoms, still more preferably 3-5 carbon atoms, and most preferably 4 carbon atoms. Most preferably, the alkylation process consists of the alkylation of isobutane with butenes.

As will be evident to the skilled person, the alkylation process can take any suitable form, including fluidized bed processes, slurry processes, and fixed bed processes. The process can be carried out in a number of beds and/or reactors, each with separate addition of alkylation agent if desirable. In such a case, the process of the invention can be carried out in each separate bed or reactor.

As mentioned above (method 3), water may be added during the process in order to increase the LOI of the catalyst to the desired level. This water can be introduced during the alkylation reaction via, e.g., the hydrocarbon feed or the feed of alkylation agent. Alternatively, the catalyst can be hydrated by using a water-containing atmosphere during the optional (mild) regeneration steps described below, or by contacting the catalyst with water in a separate intermediate hydration step.

Similar procedures can be applied to rehydrate the catalyst after its LOI has decreased during processing (i.e. during the alkylation reaction and/or regeneration).

Suitable process conditions are known to the skilled person. Preferably, an alkylation process as disclosed in WO 98/23560 is applied. The process conditions applied in the present process are summarized in the following Table:

|  | Temperature range [° C.] | Pressure range [bar] | Molar ratio of hydrocarbon to alkylation agent |
|---|---|---|---|
| Preferred | −40-250 | 1-100 | 5:1-5,000:1 |
| More preferred | 20-150 | 5-40 | 50:1-1,000:1 |
| Most preferred | 65-95 | 15-30 | 150:1-750:1 |

Optionally, in the above process the catalyst may be subjected to a high-temperature regeneration with hydrogen in the gas phase. This high-temperature regeneration is preferably carried out at a temperature of at least 150° C., more preferably at 150°-600° C., and most preferably at 200°-400° C. For details of this regeneration procedure, reference is made to WO 98/23560, and in particular to page 4, lines 12-19. This text passage is incorporated herein by reference. The high-temperature regeneration can be applied periodically during the alkylation process.

If as a result of high-temperature regeneration the water content of the catalyst has decreased to below the desired level, the catalyst may be rehydrated during the process in the ways described above, e.g. by adding water to the hydrocarbon feed or the feed of alkylation agent or by contacting the catalyst with water in a separate intermediate hydration step.

Preferably, in addition to the high-temperature regeneration treatment a milder regeneration is applied during the alkylation process, such as described in WO 98/23560, in particular page 9, line 13 through page 13, line 2. This text passage is incorporated herein by reference. More in particular, during the alkylation process the catalyst is preferably subjected intermittently to a regeneration step by being contacted with a feed containing a hydrocarbon and hydrogen, with said regeneration preferably being carried out at 90% or less, more preferably at 60% or less, even more preferably at 20% or less, and most preferably at 10% or less of the active cycle of the catalyst. The active cycle of the catalyst is defined as the time from the start of the feeding of the alkylation agent to the moment when, in comparison with the alkylation agent added to the catalyst-containing reactor section, 20% of the alkylation agent leaves the catalyst-containing reactor section without being converted, not counting isomerization inside the molecule.

The quality of the alkylate product obtained in the process according to the invention can be measured by its Research Octane Number (RON). The RON is a measure of the anti-knock rating of gasoline and/or gasoline constituents. The higher the RON, the more favourable the anti-knock rating of the gasoline will be. Depending on the type of gasoline engine, generally speaking a higher anti-knock rating is of advantage when it comes to the working of the engine. The product obtained in the process according to the invention preferably has a RON of 90 or higher, more preferably of 92 or higher, most preferably 94 or higher. The RON is obtained by determining, e.g. via gas chromatography, the percentages by volume of the various hydrocarbons in the product. The percentages by volume are then multiplied by the RON contribution and added up.

Examples of compounds with a RON of 90 or higher are isopentane, 2,2-dimethyl butane, 2,3-dimethyl butane, trimethyl butane, 2,3-dimethyl pentane, 2,2,4-trimethyl pentane, 2,2,3-trimethyl pentane, 2,3,4-trimethyl pentane, 2,3,3-trimethyl pentane, and 2,2,5-trimethyl hexane.

A related relevant parameter for product quality is the ratio of the amount of formed trimethyl pentanes (TMP) to the amount of formed dimethyl hexanes (DMH). Trimethyl pentanes have a RON of about 100-110. Dimethyl hexanes have a RON of about 60-70. Consequently, to obtain an alkylate with a high octane number, the highest possible TMP/DMH ratio is desired. The process according to the invention makes it possible to obtain a product having a TMP/DMH ratio of at least 2, preferably of at least 3, more preferably of at least 4.

As will be shown by the Examples below, the at least 1.5 wt % of water present on the catalyst results in an increase in RON and in activity such as allows the use of lower reaction temperatures to obtain the same conversion level.

FIGURES

FIG. 1 illustrates the RON at 99.5% conversion and the reaction temperature required for obtaining 99.5% conversion as a function of catalyst's $LOI_{600}$ during reaction.

Figure 2:
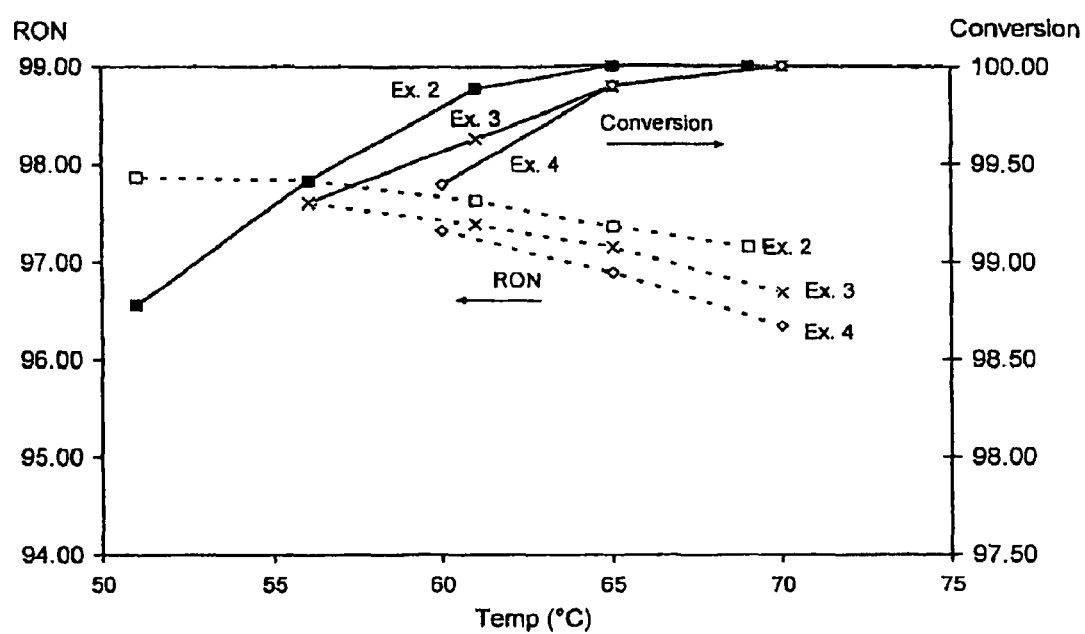

FIG. 2 displays the RON and the conversion as a function of the reaction temperature for catalysts with an $LOI_{600}$ of about 2 wt %, prepared in different ways.

EXAMPLES

General Test Procedure

A fixed-bed recycle reactor as described in WO 9823560 having a diameter of 2 cm was filled with a 1:1 volume/volume mixture of 38.6 grams of catalyst extrudates (on dry basis, i.e. the actual weight corrected for the water content) and carborundum particles (60 mesh). At the centre of the reactor tube a thermocouple of 6 mm in diameter was arranged. The reactor was flushed with nitrogen for 30 minutes (21 Nl/hour). Next, the system was tested for leakages at elevated pressure, after which the pressure was raised to 21 bar and the nitrogen replaced by hydrogen (21 Nl/hour). The reactor temperature was then raised to 275° C. at a rate of 1° C./min and the catalyst was reduced at 275° C. After 2 hours, the reactor temperature was lowered to the reaction temperature.

The hydrogen stream was stopped with the attaining of the reaction temperature. Isobutane was supplied to the reactor at a rate of about 4,000 grams/hour. About 95-98% of the isobutane was fed back to the reactor. About 2-5% was drained off for analysis. Such an amount of isobutane was supplied to the reactor as to ensure a constant quantity of liquid in the system. When the system had stabilized, such an amount of cis-2-butene was added to it as to give a cis-2-butene-WHSV of 0.19 (calculated on zeolite weight in the catalyst sample). The overall rate of flow of liquid in the system was maintained at about 4,000 g/h. The weight ratio of isobutane to cis-2-butene at the reactor inlet was about 750. The pressure in the reactor amounted to 21 bar.

Each time after 1 hour of reaction, the catalyst was regenerated by being washed with isobutane for 5 minutes, followed by 50 minutes of regeneration through being contacted with a solution of 1 mole % of $H_2$ in isobutane, and then being washed with isobutane for another 5 minutes (total washing and regeneration time 1 hour). After this washing step, alkylation was started again. The temperature during the washing steps, the regeneration step, and the reaction step was the same.

After processing as above for 24 hours at the same temperature, a pseudo-steady state was reached. Then, the temperature was decreased and the process was conducted as above for another 24 hours. Hence, the catalytic performance was measured at various temperatures going from higher to lower.

The performance was characterized by the olefin conversion per reactor pass and the research octane number (RON). The RON was determined as described on pages 13 and 14 of WO 9823560, the only exception being that the RON contribution of total C9+ (excl. 2,2,5-trimethylhexane) was estimated to be 84 instead of 90. The C5+ alkylate yield is defined as the weight amount of C5+ alkylate produced divided by the overall weight of olefin consumed.

The LOI of the catalyst was measured by measuring the catalyst's weight loss after heating for two hours at 600° C.

Example 1

A calcined catalyst comprising 70 wt % USY-zeolite, 0.34 wt % platinum, and 30 wt % alumina was contacted with ambient air for different time periods in order to increase the $LOI_{600}$ to various levels ranging from 1.7 to 10.1 wt %.

The resulting catalysts were reduced at 275° C. according to the general test procedure.

The reduced catalysts were tested in the alkylation of isobutane according to the general test procedure, using reaction temperatures up to 70° C.

After the tests, the reactor was unloaded under an inert atmosphere and the $LOI_{600}$ of the catalyst was measured, thereby correcting the weight loss for the amount of coke on the catalyst. A Leco® analyzer was used to measure the coke content. This apparatus burns the coke and measures the amount of $CO_2$ formed. The so-corrected $LOI_{600}$ of the catalysts ranged from 1.7 to 5.0.

Experiments established that the $LOI_{600}$ does not change significantly during the alkylation reaction at the conditions used. Hence, the $LOI_{600}$ measured after the reaction is considered to be the $LOI_{600}$ during the alkylation reaction.

In another experiment, the calcined catalyst was directly reduced according to the general test procedure, but at a temperature of 285° C. for 6 hours. This temperature was reached by raising the reactor temperature at a rate of 0.2° C./min. The resulting catalyst was very dry and had a $LOI_{600}$ significantly below 1.5 wt %. Exact measurement of the $LOI_{600}$ was prevented by the hygroscopic nature of the dried catalyst.

The RON at 99.5% conversion and the reaction temperature required for obtaining 99.5% conversion are plotted against the catalyst's LOI in FIG. 1. For the dry catalyst ($LOI_{600}$<1.5 wt %), the RON at 99.5% conversion was 95.5; the temperature required for obtaining 99.5% conversion was 80° C.

FIG. 1 clearly shows that the higher the water content of the catalyst, the higher the RON (i.e. the higher the selectivity) and the lower the temperature required for obtaining 99.5% conversion (i.e. the higher the activity).

Further, this figure also shows that there is an optimum in performance at an LOI between about 1.8 and 4 wt %.

Example 2

A calcined catalyst comprising 70 wt % USY-zeolite, 0.34 wt % platinum, and 30 wt % alumina was reduced at 275° C. in the manner described in the general test procedure. Then, the catalyst was unloaded from the reactor under an inert atmosphere, separated from the carborundum, and exposed to air until about 2 wt % of water was picked up.

The catalyst was again introduced into the reactor, flushed with hydrogen at 80° C. (at which temperature essentially no water will be lost from the catalyst), and the alkylation performance was investigated, according to the general test procedure.

Several experiments were conducted, each at a different temperature.

The RON and the conversion are plotted as a function of the reaction temperature in FIG. 2.

Example 3

A calcined catalyst comprising 70 wt % USY-zeolite, 0.34 wt % platinum, and 30 wt % alumina was reduced at 275° C. in the manner described in the general test procedure. Then, the catalyst was unloaded from the reactor under an inert atmosphere, separated from the carborundum, and exposed to air until 7.7 wt % of water was picked up.

The catalyst was again introduced into the reactor, and reduced again at 275° C. in the manner described in the general test procedure. This resulted in a decrease of the LOI to about 2 wt %. Next, the alkylation performance was investigated according to the general test procedure.

Several experiments were conducted, each at a different temperature.

The RON and the conversion are plotted as a function of the reaction temperature in FIG. 2.

Example 4

A calcined catalyst comprising 70 wt % USY-zeolite, 0.34 wt % platinum, and 30 wt % alumina was contacted with ambient air to obtain an $LOI_{600}$ of about 4.1 wt %. The catalyst was then reduced and tested according to the general test procedure. The $LOI_{600}$ after reduction and before starting the alkylation reaction amounted about 2 wt %.

Several experiments were conducted, each at a different temperature.

The RON and the conversion are plotted as a function of the reaction temperature in FIG. 2.

From FIG. 2 it can be seen that the highest conversion and the highest RON are obtained with a catalyst wetted according to Example 2, while a catalyst wetted according to Example 4 shows the lowest activity and RON.

The invention claimed is:

1. A process for alkylating a hydrocarbon feed which comprises contacting the a hydrocarbon feed to be alkylated with an alkylation agent in the presence of a catalyst comprising a solid acid, a hydrogenation metal, and 1.5-6 wt % of water, measured as the loss on ignition at 600° C., wherein said catalyst contains no halogen component.

2. The process according to claim 1 wherein the catalyst comprises 1.8-4 wt % of water.

3. The process according to claim 2 wherein the catalyst comprises 2-3 wt % of water.

4. The process according to claim 1 wherein the solid acid is selected from the group consisting of zeolites and mixtures thereof.

5. The process according to claim 4 wherein the solid acid is a zeolite selected from the group consisting of mordenite, zeolite beta, X-zeolites, and Y-zeolites.

6. The process according to claim 1 wherein the hydrogenation metal is a Group VIII noble metal.

7. The process according to claim 1, wherein the hydrocarbons are saturated hydrocarbons.

8. The process according to claim 1 wherein the catalyst is prepared by adding water to a dry catalyst comprising solid acid and hydrogenation metal before use in the alkylation process.

9. The process according to claim 1 wherein the alkylation process is started using a catalyst comprising less than 1.5 wt % water and wherein water is added to the catalyst during the alkylation process.

10. The process according to claim 1 wherein water is added to the catalyst during the alkylation process by exposing a regenerated catalyst to a water-containing atmosphere, or by using a water-containing atmosphere during a regeneration step.

* * * * *